United States Patent
De Barros Sanches et al.

(10) Patent No.: US 11,304,883 B2
(45) Date of Patent: Apr. 19, 2022

(54) POLISHED TALC MICROBEADS

(71) Applicant: MONDO MINERALS B.V., Amsterdam (NL)

(72) Inventors: Jose Manuel De Barros Sanches, Zaandam (NL); Tomasz Wasilewski, Radom (PL); Anna Maria Kanios-Zakrzewska, Amsterdam (NL)

(73) Assignee: MONDO MINERALS B.V., Amsterdam (NL)

( * ) Notice: Subject to any disclaimer, the term of this patent is extended or adjusted under 35 U.S.C. 154(b) by 0 days.

(21) Appl. No.: 16/339,814

(22) PCT Filed: Oct. 14, 2016

(86) PCT No.: PCT/EP2016/074729
§ 371 (c)(1),
(2) Date: Apr. 5, 2019

(87) PCT Pub. No.: WO2018/068865
PCT Pub. Date: Apr. 19, 2018

(65) Prior Publication Data
US 2019/0307660 A1 Oct. 10, 2019

(51) Int. Cl.
*A61K 8/25* (2006.01)
*A61K 8/02* (2006.01)
*A61K 8/44* (2006.01)
*A61K 8/46* (2006.01)
*A61Q 11/00* (2006.01)
*A61Q 19/10* (2006.01)
*C01B 33/22* (2006.01)

(52) U.S. Cl.
CPC .............. *A61K 8/25* (2013.01); *A61K 8/0241* (2013.01); *A61K 8/442* (2013.01); *A61K 8/447* (2013.01); *A61K 8/466* (2013.01); *A61Q 11/00* (2013.01); *A61Q 19/10* (2013.01); *C01B 33/22* (2013.01); *A61K 2800/28* (2013.01); *A61K 2800/41* (2013.01); *A61K 2800/412* (2013.01); *C01P 2004/02* (2013.01); *C01P 2004/60* (2013.01)

(58) Field of Classification Search
None
See application file for complete search history.

(56) References Cited

U.S. PATENT DOCUMENTS 3,939,249 A 2/1976 Huege
5,849,333 A * 12/1998 Nordhauser ............ A61K 8/25
424/489
8,729,137 B2 * 5/2014 Misner .................... A61K 8/25
514/770

FOREIGN PATENT DOCUMENTS

JP 2006143681 A 6/2006
JP 2008239792 A 10/2008
JP 2014043420 A 3/2014

OTHER PUBLICATIONS

Filio et al (Powder Technology 78:121-127, 1994) (Year: 1994).*
Fiume et al (Int J Toxicol 34(Suppl I) 66S-129S, published Jul. 30, 2015) (Year: 2015).*
U.S. Food & Drug Administration (available online at https://www.fda.gov/cosmetics/cosmetic-products/frequently-asked-questions-soap)—accessed Jun. 18, 2021 (Year: 2021).*
Soap Queen ("Understanding FDA Cosmetic vs. Drug Claims", available on https://www.soapqueen.com/business/understanding-fda-cosmetic-vs-drug-claims/, Sep. 9, 2015) (Year: 2015).*
International Search Report and Written Opinion for the International Patent Application No. PCT/EP2016/074729, dated Jan. 11, 2017, 12 pages.
J.M. Filio et al., "A study on talc ground by tumbling and planetary ball mills", Powder Technology, vol. 78m 1994, pp. 121-127, XP002764464, the whole document.
Imerys: "Imercare P-Scrub—A new gentle volcanic rock-based exfoliant for scrub applications", Jul. 2010 (Jul. 2010), pp. 1-6, XP002764465, Retrieved from the Internet: URL: http://www.imerys-perfmins.com/pdf/TB.ImerCarePScrubPeriiteforScrubApplications.May 2016.pdf [retrieved on Nov. 17, 2016] the whole document.
George Deckner: "Finding Alternatives to Synthetic Exfoliating Beads" Prospector, Feb. 28, 2014 (Feb. 28, 2014), XP002764466, Retrieved from the Internet: URL: http://knowledge.ulprospector.com/369/pcc-finding-alternatives-synthetic-exfoliating-beads/ [retrieved on Nov. 17, 2016] the whole document.
"Talc"—An Overview | Science Direct. Retrieved Nov. 27, 2020, 12 pages.
Castillo et al., "Particulate Science and Technology: An International Journal" Taylor & Francis, Apr. 23, 2013, 32 pages.

* cited by examiner

*Primary Examiner* — Craig D Ricci
(74) *Attorney, Agent, or Firm* — Kacvinsky Daisak Bluni PLLC

(57) ABSTRACT

Polished talc microbeads, i.e. polished talc particles with a largest average diameter of less than 500 μm and methods for the preparation thereof, which microbeads are especially suitable to be use as an alternative for plastic microbeads used in cosmetics and personal hygiene products. Body scrubs, tooth pastes and soaps comprising the present polished talc microbeads. The use of polished talc microbeads with a talc content of more than 70% (w/w) and a largest diameter of less than 500 μm as a substitute for plastic microbeads in cosmetics and personal hygiene products.

10 Claims, 1 Drawing Sheet

POLISHED TALC MICROBEADS

This is a national stage application filed under 35 U.S.C. § 371 of pending international application PCT/EP2016/074729 filed Oct. 14, 2016 the entirety of which application is hereby incorporated by reference herein.

The present invention relates to polished talc microbeads, i.e. polished talc particles with a largest average diameter of less than 500 μm and to methods for the preparation thereof. The present polished talc microbeads are especially suitable to be use as an alternative for plastic microbeads, such as polyethylene microbeads, used in cosmetics and personal hygiene products. Accordingly, the present invention additionally relates to body scrubs, tooth pastes and soaps comprising the present polished talc microbeads.

Presently, microbeads are solid plastic particles of less than 0.5 millimetres in their largest dimension. They are generally made of polyethylene but can be of other plastics such as polypropylene and polystyrene. Microbeads have been used in personal care products, cosmetics and toothpastes as well as in biomedical and health science research. Sphericity and particle size uniformity create a ball-bearing effect in creams and lotions, resulting in a silky texture and spreadability. Smoothness and roundness provide lubrication.

Microbeads, after use, are generally washed down the drain and can pass unfiltered through the sewage treatment plants ultimately making their way into rivers and canals, resulting in plastic particle water pollution. The beads can absorb and concentrate pollutants like pesticides and polycyclic hydrocarbons. Microbeads have been found to pollute the Great Lakes in high concentrations, particularly Lake Erie. A study from the State University of New York, found anywhere from 1500 to 1 million microbeads per square mile on the surface of the Great Lakes.

Due to the increase in bans of microbeads in many countries such as the USA and in Europe, many cosmetic companies are phasing out microbeads from their production lines for exfoliates, cleansers and shower gels.

Considering the above, there is a clear need in the art for alternatives of plastic microbeads being readily applicable in cosmetics and personal hygiene products and being environmental friendly.

It is an object of the present invention, amongst other objects, to meet the above need in the art.

This object of the present invention, amongst other objects is met as outlined in the appended claims.

Specifically, this object of the present invention, amongst other objects, is met, according to a first aspect, by the use of polished talc microbeads with a talc content of more than 70% (w/w) such as 80%, 90%, 91%, 92%, 93%, 94%, 95% as 96%, 97%, 98%, 99% and substantially 100%, and a largest diameter of less than 500 μm as substitute for plastic microbeads in cosmetics and personal hygiene products.

The present inventors have surprisingly found that relatively small talc particles, i.e. less than 500 μm, of sufficient purity, i.e. >75% (w/w) can provide a suitable alternative for plastic microbeads. However, such talc particles can only provide an alternative if sufficiently spherical and smooth, or formulated differently, sufficiently polished. According to the invention, such polishing can be readily obtained by adding sieved talc particles of less than 500 μm into a revolving drum and allowing the talc particles to tumble, i.e. to roll over. Although a specific time frame depends on process conditions, suitable time frames to be contemplated are 5 minutes to 2 hours.

Considering the above, the present invention, according to a second aspect, relates to a method for providing polished talc microbeads, the method comprises the steps of:
 a) providing course talc with a talc content of at least 70, preferably at least 95% and an average largest diameter of between 1 cm to 10 cm;
 b) crushing the course talc particles;
 c) sieving the crushed talc particles through a sieve thereby obtaining talc particles with an average largest diameter of less than 500 μm;
 d) subjecting the sieved talc particles to tumbling thereby obtaining polished talc microbeads.

According to the present invention, polished talc microbeads with a largest diameter between 500 μm and 250 μm can be used in a body scrub; polished talc microbeads with a largest diameter between 250 μm and 125 μm can be used in a facial scrub; and polished talc microbeads with a largest diameter is between 125 μm and 0.5 μm such as 90 μm can be used in tooth paste, creams and soaps.

According to the present invention, polished talc particles can also be used in a liquid, i.e. water based, soap in an amount of 1% to 5% (w/w) in combination with one or more surfactants in an amount of 1% to 15% (w/w).

According to the present invention, the present polished talc particles can also be used in a dry soap comprising more than 50% (w/w/) of the present polished talc microbeads in combination with one or more surfactants.

The present invention will be further detailed in the following examples of preferred embodiments of the present invention. In the examples, reference is made to a FIG. 1 wherein:

FIG. 1: shows a 30× magnification of the present polished talc microbeads after tumbling (right) and before tumbling (left).

EXAMPLES

Example 1: General Preparation of the Polished Talc Microbeads

Coarse talc (hydrated magnesium silicate) of less than 10 cm diameter was subjected to crushing and subsequently sieved to obtain a fractions with 1) an average largest diameter of 500 to 250 μm; 2) an average largest diameter of 250 to 125 μm; 3) an average largest diameter of 125 to 90 μm and 4) an average largest diameter of less than 90 μm. Subsequently, the fractions were added into a rotating drum and allowed to tumble at 60 rpm for 20 minutes in order to polish the talc particles. A representative example of the 500 to 250 μm fraction before (left) and after (right) tumbling is shown in FIG. 1. As can be seen in FIG. 1, tumbling provides smoothness and roundness to the talc particles and, additionally, provides a more spherical shape.

Example 2: Powdered Soap (Dry Soap)

Three formulations of a powdered (dry) soap were prepared by mixing the constituting ingredients in any given order:

| Fomulation 1 | | |
| --- | --- | --- |
| Compound | Amount in percentage (w/w) | Function |
| Sodium lauryl sulfoacetate | 26 | Surfactant |
| Polished talc | ad 100 | fraction less than 250 μm |

Formulation 1

| Compound | Amount in percentage (w/w) | Function |
| --- | --- | --- |
| Sorbitol | 5 | Humectant |
| Citric acid monohydrate | 0.3 | Buffer |

Formulation 2

| Compound | Amount in percentage (w/w) | Function |
| --- | --- | --- |
| Sodium lauryl sarcosinate | 24.7 | Surfactant |
| Polished talc | ad 100 | fraction less than 250 μm |
| Citric acid | 0.3 | Buffer |
| Sodium methyl cocoyl taurate | 5.2 | Surfactant |

Formulation 3

| Compound | Amount in percentage (w/w) | Function |
| --- | --- | --- |
| Sodium lauryl sulfoacetate | 23.0 | Surfactant |
| Polished talc | ad 100 | fraction less than 250 μm |
| Citric acid | 0.3 | Buffer |
| Sodium methyl cocoyl taurate | 5.7 | Surfactant |
| Sorbitol | 5.0 | Humectant |
| Allantoin | 0.2 | Skin soothing and protection |
| Urea | 0.3 | Skin conditioning |

Example 3: Liquid Soap

Formulation liquid soap

| Compound | Amount in percentage (w/w) | Function |
| --- | --- | --- |
| Aqua | Ad 100 | Solvent |
| Acrylates/C10-30 Alkyl Acrylate Crosspolymer | 0.8 | Viscosity modifier |
| Sodium Lauroyl Sarcosinate | 5.13 | Surfactant |
| Sodium Laureth Sulfate | 2.7 | Surfactant |
| Cocamidopropyl Betaine | 0.9 | Surfactant |
| Triethanolamine | q.s. | buffer |
| Polished talc | 2.5 | fraction less than 250 μm |

Manufacturing Procedure:

Heat water of phase A up to 40° C. Add Acrylates/C10-30 Alkyl Acrylate Crosspolymer while stirring and homogenize for 1 to 2 min. to ensure complete hydration. Mix the remained of the ingredients and adjust the pH with triethanolamine to 6.8. Stir with moderate speed until a homogenous gel is obtained.

Appearance: milky homogenous gel
pH-Value: 6.8
Viscosity (Brookfield RVDVI, spindle 3, speed 10 rpm) mPa·s: 4500-7000
Stability: more than 3 months.

The invention claimed is:

1. A liquid soap consisting of:
   (a) spherical and smooth talc microbeads in an amount of 1% to 5% (w/w);
   (b) surfactant; and
   (c) water;
   wherein the talc microbeads have a talc content of at least 75% (w/w); and the largest diameter of the talc microbeads is 500 μm or less.

2. The liquid soap of claim 1, wherein the largest diameter of the talc microbeads is between 250 μm and 500 μm.

3. The liquid soap of claim 1, wherein the largest diameter of the talc microbeads is between 125 μm and 250 μm.

4. The liquid soap of claim 1, wherein the largest diameter of the talc microbeads is between 0.5 μm and 125 μm.

5. The liquid soap of claim 1, wherein the amount of surfactant is between 1% and 15% (w/w).

6. A dry soap consisting of:
   (a) spherical and smooth talc microbeads in an amount of at least 50% (w/w); and
   (b) surfactant;
   wherein the talc microbeads have a talc content of at least 75% (w/w); and the largest diameter of the talc microbeads is 500 μm or less.

7. The dry soap of claim 6, wherein the largest diameter of the talc microbeads is between 250 μm and 500 μm.

8. The dry soap of claim 6, wherein the largest diameter of the talc microbeads is between 125 μm and 250 μm.

9. The dry soap of claim 6, wherein the largest diameter of the talc microbeads is between 0.5 μm and 125 μm.

10. The dry soap of claim 6, wherein the amount of surfactant is at least 15% (w/w).

* * * * *